United States Patent
Aradachi

(10) Patent No.: US 12,011,048 B2
(45) Date of Patent: *Jun. 18, 2024

(54) AEROSOL GENERATION SYSTEM

(71) Applicant: Japan Tobacco Inc., Tokyo (JP)

(72) Inventor: Takao Aradachi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,629

(22) Filed: Aug. 8, 2022

(65) Prior Publication Data

US 2022/0378112 A1 Dec. 1, 2022

Related U.S. Application Data

(63) Continuation of application No. 17/464,679, filed on Sep. 2, 2021, now Pat. No. 11,445,764.

(30) Foreign Application Priority Data

Sep. 7, 2020 (JP) .................................. 2020-150108

(51) Int. Cl.
*A24F 40/90* (2020.01)
*A24F 40/46* (2020.01)
(Continued)

(52) U.S. Cl.
CPC .............. *A24F 40/90* (2020.01); *A24F 40/46* (2020.01); *H02J 7/007* (2013.01);
(Continued)

(58) Field of Classification Search
CPC ........ H02J 7/007; H02J 7/342; H02J 7/00041; H02J 7/00043; H02J 7/00712; A24F 40/46; A24F 40/53; A24F 40/57; A24F 40/90

(Continued)

(56) References Cited

U.S. PATENT DOCUMENTS 11,122,837 B2 * 9/2021 Mizuguchi .............. A24F 40/90
11,445,764 B2 * 9/2022 Aradachi .............. A61M 15/06
(Continued)

FOREIGN PATENT DOCUMENTS

JP 2019-524069 A 9/2019
KR 10-2019-0120802 A1 10/2019
(Continued)

OTHER PUBLICATIONS

Notice of Reasons for Refusal dated Dec. 11, 2020, received for JP Application 2020-150108, 9 pages.
(Continued)

*Primary Examiner* — Edward Tso
*Assistant Examiner* — Aaron Piggush
(74) *Attorney, Agent, or Firm* — XSENSUS LLP

(57) ABSTRACT

The present invention provides an aerosol generation system comprising: a controller for an inhalation device, the controller including a first power supply, a first connector, and a first processor configured to perform energization control of a heater which is used to heat an aerosol source, and a power supply device including a second power supply, a second connector which is connected to the first connector at the time of charging of the first power supply, and a second processor configured to perform control of power supply from the second power supply to the controller via the second connector, wherein a first voltage applied to a power supply terminal of the first processor and a second voltage applied to a power supply terminal of the second processor are different from each other.

10 Claims, 7 Drawing Sheets

(51) Int. Cl.
  *H02J 7/00* (2006.01)
  *A24F 40/53* (2020.01)
  *A24F 40/57* (2020.01)
  *H02J 7/34* (2006.01)

(52) U.S. Cl.
  CPC ............ *H02J 7/00712* (2020.01); *A24F 40/53* (2020.01); *A24F 40/57* (2020.01); *H02J 7/342* (2020.01)

(58) Field of Classification Search
  USPC .......... 320/107, 114, 138, 162, 163; 131/329
  See application file for complete search history.

(56) References Cited

U.S. PATENT DOCUMENTS

| | | | | |
|---|---|---|---|---|
| 2005/0052196 | A1* | 3/2005 | Borkar | H01L 23/34 |
| | | | | 257/E23.08 |
| 2019/0013960 | A1* | 1/2019 | Sadwick | H05B 47/19 |
| 2019/0387806 | A1* | 12/2019 | Nakano | A24F 40/50 |
| 2020/0237006 | A1* | 7/2020 | Akao | A24F 40/51 |
| 2020/0237011 | A1* | 7/2020 | Akao | G01R 31/392 |
| 2020/0245688 | A1* | 8/2020 | Yamada | A24F 40/60 |
| 2020/0352254 | A1 | 11/2020 | Yamada et al. | |
| 2020/0358300 | A1 | 11/2020 | Akao et al. | |
| 2020/0375260 | A1 | 12/2020 | Mizuguchi et al. | |
| 2022/0287373 | A1* | 9/2022 | Lin | A24F 40/60 |

FOREIGN PATENT DOCUMENTS

| | | |
|---|---|---|
| WO | 2018/001910 A1 | 1/2018 |
| WO | 2019/082249 A1 | 5/2019 |
| WO | 2019/150545 A1 | 8/2019 |
| WO | 2019/150546 A1 | 8/2019 |

OTHER PUBLICATIONS

Decision to Grant dated Mar. 29, 2021, received for JP Application 2020-150108, 5 pages.
Korean Office Action dated Jan. 13, 2022 in Korean Application No. 10-2021-0110691.

* cited by examiner

AEROSOL GENERATION SYSTEM

CROSS-REFERENCE TO RELATED APPLICATIONS

This application is a continuation of U.S. application Ser. No. 17/464,679, filed Sep. 2, 2021, which claims priority to and the benefit of Japanese Patent Application No. 2020-150108 filed on Sep. 7, 2020, the entire disclosure of each are incorporated herein by reference.

BACKGROUND OF THE INVENTION

Field of the Invention

The present invention relates to an aerosol generation system.

Description of the Related Art

Japanese Patent Laid-Open No. 2019-524069 describes an aerosol generation system comprising an aerosol generation device that generates an aerosol by heating an aerosol forming substance by a heater, and a charging device (to be also referred to as a power supply device) including a battery and used to charge the aerosol generation device.

In the aerosol generation system, operating the processor of the aerosol generation device and the processor of the charging device (power supply device) in similar manners even though they are performing different processes can be disadvantageous in terms of power saving.

SUMMARY OF THE INVENTION

The present invention provides, for example, a technique advantageous in power saving of an aerosol generation system.

According to one aspect of the present invention, there is provided an aerosol generation system comprising: a controller for an inhalation device, the controller including a first power supply, a first connector, and a first processor configured to perform energization control of a heater which is used to heat an aerosol source, and a power supply device including a second power supply, a second connector which is connected to the first connector at the time of charging of the first power supply, and a second processor configured to perform control of power supply from the second power supply to the controller via the second connector, wherein a first voltage applied to a power supply terminal of the first processor such that the first processor can perform the energization control and a second voltage applied to a power supply terminal of the second processor such that the second processor can perform the control of the power supply are different from each other.

Further features of the present invention will become apparent from the following description of exemplary embodiments with reference to the attached drawings.

DESCRIPTION OF THE EMBODIMENTS

Figure 1:
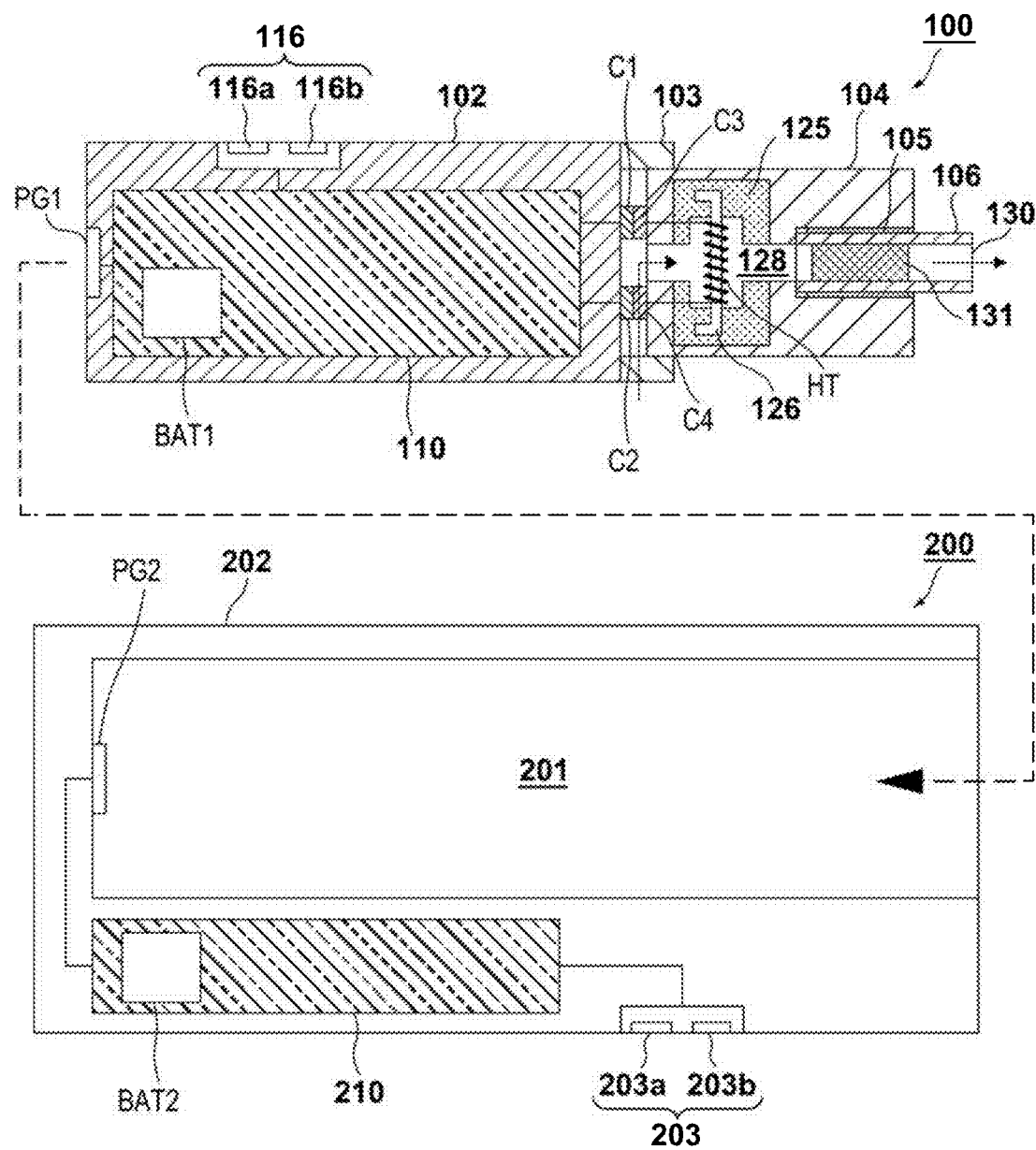
FIG. 1 is a view schematically showing an arrangement example of an aerosol generation system.

Hereinafter, embodiments will be described in detail with reference to the attached drawings. Note that the following embodiments are not intended to limit the scope of the claimed invention, and limitation is not made an invention that requires all combinations of features described in the embodiments. Two or more of the multiple features described in the embodiments may be combined as appropriate. Furthermore, the same reference numerals are given to the same or similar configurations, and redundant description thereof is omitted.

FIG. 1 schematically shows an arrangement example of an aerosol generation system according to an embodiment. The aerosol generation system can include an inhalation device 100 and an external power supply (power supply device) 200.

The inhalation device 100 can be configured to provide, to a user via a mouthpiece port 130, a gas containing an aerosol, a gas containing an aerosol and a flavor material, an aerosol, or an aerosol containing a flavor material in accordance with an operation requesting the aerosol (to be also referred to as an atomization request hereinafter) such as an inhalation operation by the user. The inhalation device 100 can comprise a controller 102 and an atomizer 104. The inhalation device 100 can comprise a holding portion 103 that detachably holds the atomizer 104. The controller 102 may be understood as a controller for an inhalation device. The atomizer 104 can be configured to atomize an aerosol source. The aerosol source can be, for example, a liquid such as a multivalent alcohol such as glycerin or propylene glycol. Alternatively, the aerosol source may contain a drug. The aerosol source can be a liquid, a solid, or a mixture of a liquid and a solid. A vapor source such as water may be used in place of the aerosol source.

The inhalation device 100 may further comprise a capsule 106 containing a flavor source 131. The atomizer 104 can include a capsule holder 105 that detachably holds the capsule 106. The capsule holder 105 may be included not in the atomizer 104 but in the controller 102. The flavor source 131 can be a molded body obtained by molding, for example, a cigarette material. Alternatively, the flavor source 131 may be made of a plant (for example, mint, herb, Chinese medicine, coffee beans, or the like) except the cigarette. A fragrance such as menthol may be added to the flavor source. The flavor source 131 may be added to an aerosol source. The atomizer 104 and the capsule holder 105 may be integrally formed in place of an arrangement in which the inhalation device 100 or the atomizer 104 includes the capsule holder 105.

The controller 102 can comprise electrical components 110 including a first power supply BAT1. The first power supply BAT1 may be formed by a secondary battery such as a lithium ion secondary battery, or an electric double-layer capacitor such as a lithium ion capacitor. The electrical components 110 can include a user interface 116. Alternatively, the controller 102 may be understood to include the electrical components 110 and the user interface 116. The user interface 116 can include, for example, a display unit 116a (for example, a light emitting device such as an LED and/or an image display unit such as an LCD) that provides the user with information and/or an operation unit 116b (for example, a switch such as a button switch and/or a touch display) that accepts a user operation. The controller 102 can comprise a first connector PG1 which is electrically connected to a second connector PG2 of the external power supply when the controller 102 is accommodated in an accommodation portion 201 of the external power supply 200, thereby enabling charging by the external power supply 200. The first connector PG1 is not necessarily physically connected to the second connector PG2 to enable charging by the external power supply 200. For example, the second connector PG2 may supply power, in a non-contact manner, to the first connector PG1 which is not physically connected thereto. The first connector PG1 is electrically connected to the electrical components 110. In the example shown in FIG. 1, the first connector PG1 is provided at a position opposite to the position where the atomizer 104 is provided in the controller 102, but the position of the first connector PG1 in the controller 102 can be arbitrary. The first connector PG1 may be a female (concave type) receptacle and the second connector PG2 may be a male (convex type) plug. Alternatively, the first connector PG1 may be a male (convex type) plug and the second connector PG2 may be a female (concave type) receptacle.

The holding portion 103 of the controller 102 can include a first electrical contact C1 and a second electrical contact C2. In a state in which the atomizer 104 is held by the holding portion 103, the first electrical contact C1 of the holding portion 103 can contact a third electrical contact C3 of the atomizer 104, and the second electrical contact C2 of the holding portion 103 can contact a fourth electrical contact C4 of the atomizer 104. The controller 102 can supply power to the atomizer 104 (heater HT) via the first electrical contact C1 and the second electrical contact C2.

The atomizer 104 can include the third electrical contact C3 and the fourth electrical contact C4 described above. In addition, the atomizer 104 can include the heater HT for heating and atomizing the aerosol source, a container 125 for holding the aerosol source, and a transport portion (wick) 126 for transporting the aerosol source held by the container 125 to a heating region of the heater HT and holding the aerosol source in the heating region. At least part of the heating region can be arranged in a channel 128 formed in the atomizer 104. The first electrical contact C1, the third electrical contact C3, the heater HT, the fourth electrical contact C4, and the second electrical contact C2 form a current path for flowing the current to the heater HT. The transport portion 126 can be made of, for example, a fiber element such as a glass fiber, a porous material such as a ceramic, or a combination thereof. Note that the means for transporting the aerosol source held in the container 125 to the heating region is not limited to the wick, but a spraying device such as a spray or a transporting means such as a pump may be used instead.

As described above, the atomizer 104 can include the capsule holder 105 for detachably holding the capsule 106. As an example, the capsule holder 105 can hold the capsule 106 such that part of the capsule 106 is accommodated in the capsule holder 105 or the atomizer 104 and the remaining part of the capsule 106 including the mouthpiece port 130 is exposed. The user can hold the mouthpiece port 130 with his/her mouth and suck the gas containing the aerosol or the aerosol. Since the mouthpiece port 130 is included in the detachable capsule 106 as described above, the inhalation device 100 can be kept clean.

When the user holds the mouthpiece port 130 with his/her mouth and performs the inhalation operation, as exemplified by a solid arrow in FIG. 1, air flows into the channel 128 of the atomizer 104 through an opening (not shown). When the heater HT heats the aerosol source, the vaporized and/or aerosolized aerosol source is transported toward the mouthpiece port 130 with the air. In the process in which the aerosol source is transported toward the mouthpiece port 130, the vaporized and/or aerosolized aerosol source is cooled to form fine liquid droplets. This can promote aerosolization. In the arrangement in which the flavor source 131 is arranged, the flavor material generated by the flavor source 131 is added to this aerosol, and the resultant material is transported to the mouthpiece port 130, thus allowing the user to suck the aerosol containing the flavor material. Since the flavor material generated by the flavor source 131 is added to the aerosol, the flavor material can be efficiently transported to the lungs of the user without staying in the oral cavity.

The external power supply 200 can be configured to supply power to the controller 102 to charge the first power supply BAT1 included in the controller 102 of the inhalation device 100. The external power supply 200 according to this embodiment is, for example, a portable pocket charger, and can be sized to fit in a clothing pocket or bag of the user. The external power supply 200 can comprise a housing 202 including the accommodation portion 201 (accommodation space) where the inhalation device 100 can be accommodated, a user interface 203, and electrical components 210 including a second power supply BAT2. The second power supply BAT2 may be formed by a secondary battery such as a lithium ion secondary battery, or an electric double-layer capacitor such as a lithium ion capacitor. The user interface 203 can include, for example, a display unit 203a (for example, a light emitting device such as an LED and/or an image display unit such as an LCD) that provides the user with information and/or an operation unit 203b (for example, a switch such as a button switch and/or a touch display) that accepts a user operation. The electrical components 210 are provided in the housing 202.

As indicated by a dashed arrow in FIG. 1, the controller 102 of the inhalation device 100 is inserted into the accommodation portion 201 of the external power supply 200. The housing 202 of the external power supply 200 may be configured so as to allow the controller 102 holding the atomizer 104 (the capsule 106 may be attached thereto) to be accommodated in the accommodation portion 201, or may be configured so as to allow the controller 102 alone to be accommodated in the accommodation portion 201. The external power supply 200 can further include, in the accommodation portion 201, the second connector PG2 which is electrically connected to the first connector PG1 of the controller 102 when the controller 102 is accommodated in the accommodation portion 201. Here, the external power supply 200 may comprise a terminal (not shown) such as a USB (Universal Serial Bus) which is electrically connected to, for example, a home power supply to charge the second power supply BAT2 of the external power supply 200. The external power supply 200 may further comprise, in the housing 202, a lid member (not shown) which is configured to be openable/closable with respect to the accommodation portion 201 so as to cover the controller 102 accommodated in the accommodation portion 201.

Figure 2:
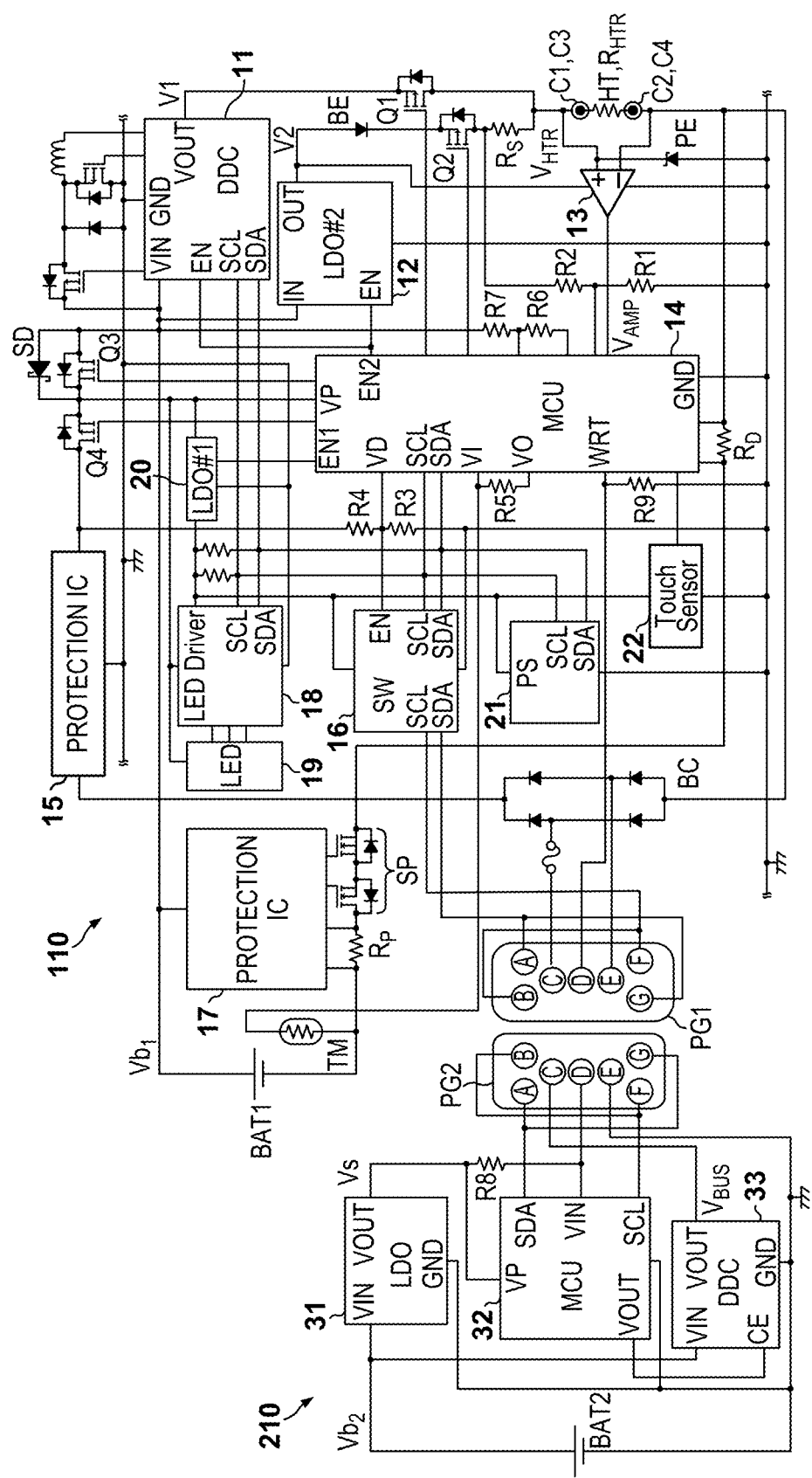
FIG. 2 is a view showing an arrangement example of electrical components of a controller and an arrangement example of electrical components of an external power supply.

FIG. 2 shows an arrangement example of the electrical components 110 of the controller 102 and an arrangement example of the electrical components 210 of the external power supply 200. FIG. 2 also shows the first connector PG1 of the controller 102 and the second connector PG2 of the external power supply 200. Each of the first connector PG1 and the second connector PG2 includes electrical contacts A to G. When the controller 102 is inserted into the accommodation portion 201 of the external power supply 200 and the first connector PG1 is connected to the second connector PG2, the electrical contacts of the first connector PG1 can contact the electrical contacts of the second connector PG2 such that the electrical contacts with the same reference symbols contact each other. Here, in the aerosol generation system according to this embodiment, the controller 102 can be inserted into the accommodation portion 201 of the external power supply 200 in a state in which the orientation of the controller 102 is inverted in the vertical direction in the drawing in FIG. 1. In this case, the electrical contacts A to G of the first connector PG1 contact the electrical contacts G to A of the second connector PG2, respectively. However, even in this case, the controller 102 and the external power supply 200 can be normally operated by the circuit arrangement shown in FIG. 2.

First, the arrangement example of the electrical components 110 of the controller 102 will be described. The electrical components 110 can include, for example, the first power supply BAT1, a power supply unit that supplies power to the atomizer 104 (heater HT thereof), a detection unit for detecting the resistance value of the heater HT, and an energization control unit that controls energization of the heater HT in accordance with the information obtained by the detection unit. The heater HT has a resistance value $R_{HTR}$ that changes in accordance with the temperature of the heater HT. The resistance value may have a positive temperature coefficient characteristic (so-called PTC characteristic) and increase as the temperature of the heater HT increases, or may have a negative temperature coefficient characteristic (so-called NTC characteristic) and increase as the temperature of the heater HT decreases. As has been described above, the third electrical contact C3 of the heater HT contacts the first electrical contact C1 of the controller 102, and the fourth electrical contact C4 of the heater HT contacts the second electrical contact C2 of the controller 102.

The power supply unit that supplies power to the heater HT can include a voltage converter 11 and a switch Q1. The voltage converter 11 includes, for example, a DC/DC converter. The voltage converter 11 converts a voltage $Vb_1$ supplied from the plus terminal of the first power supply BAT1 into a heater driving voltage V1, and outputs it from an output terminal VOUT. The heater driving voltage V1 output from the output terminal VOUT of the voltage converter 11 is supplied to the first electrical contact C1 contacting the third electrical contact C3 of the heater HT. Since the second electrical contact C2 contacting the fourth electrical contact C4 of the heater HT is electrically connected to the minus terminal of the first power supply BAT1, the current path for flowing the current to the heater HT can be formed between the output terminal VOUT of the voltage converter 11 and the minus terminal of the first power supply BAT1. The generated amount of aerosol tends to increase as the voltage applied to the heater HT is higher. Therefore, the voltage converter 11 preferably includes a boost DC/DC converter or a buck-boost DC/DC converter. The switch Q1 includes, for example, a field effect transistor (FET), and opening/closing (ON/OFF) of the switch Q1 can be controlled by a first processor 14. The switch Q1 can be arranged on the line (current path) connecting the output terminal VOUT of the voltage converter 11 and the heater HT (first electrical contact C1), but the present invention is not limited to this, and the switch Q1 may be arranged on the line connecting the heater HT (second electrical contact C2) and the minus terminal of the first power supply BAT1. Note that the diode added to the switch Q1 in FIG. 2 represents the body (parasitic) diode of the field effect transistor.

The detection unit for detecting the resistance value $R_{HTR}$ of the heater HT can include a voltage conversion circuit 12 and an amplifier 13. The voltage conversion circuit 12 includes, for example, a linear regulator such as an LDO (Low DropOut) regulator. The voltage conversion circuit 12 converts the voltage $Vb_1$ supplied from the plus terminal of the first power supply BAT1 into a detection voltage V2 for detecting the resistance value $R_{HTR}$ of the heater HT, and outputs it from an output terminal VOUT. The amplifier 13 can include, for example, an operational amplifier which includes a noninverting input terminal, an inverting input terminal, and an output terminal. The positive power supply terminal of the amplifier 13 can be connected to the output terminal VOUT of the voltage conversion circuit 12, and the negative power supply terminal thereof can be connected to the ground line. The noninverting input terminal of the amplifier 13 is connected to the first electrical contact C1, and the inverting input terminal thereof is connected to the second electrical contact C2. Accordingly, the potential difference between the first electrical contact C1 and the second electrical contact C2, that is, a voltage $V_{HTR}$ of the heater HT is input to the amplifier 13. An output voltage $V_{AMP}$ of the amplifier 13 can be input to the first processor 14. Note that in the example shown in FIG. 2, a Zener diode PE is provided between the noninverting input terminal of the amplifier 13 and the ground line. The Zener diode PE is used to suppress an unexpected operation or failure of the amplifier 13 caused by an input of an excessive voltage to the noninverting input terminal of the amplifier 13.

The detection unit for detecting the resistance value $R_{HTR}$ of the heater HT can further include a switch Q2 and a shunt resistor Rs ("Rs" may also refer to the resistance value of the shunt resistor Rs hereinafter). Assume that the resistance value of the shunt resistor Rs hardly changes even when the temperature of the shunt resistor Rs changes. The switch Q2 includes, for example, a field effect transistor (FET), and opening/closing (ON/OFF) of the switch Q2 can be controlled by the first processor 14. The switch Q2 can be arranged on the line connecting the output terminal VOUT of the voltage conversion circuit 12 and the heater HT (first electrical contact C1), but the present invention is not limited to this, and the switch Q2 may be arranged on the line connecting the heater HT (second electrical contact C2) and the minus terminal of the first power supply BAT1. A diode BE can be provided on the line connecting the output terminal VOUT of the voltage conversion circuit 12 and the switch Q2. The shunt resistor Rs can be arranged on the line connecting the switch Q2 and the heater HT in series with the switch Q2. Note that the diode added to the switch Q2 in FIG. 2 represents the body (parasitic) diode of the field effect transistor. In the example shown in FIG. 2, resistors R1 and R2 arranged in series are provided between the line connecting the switch Q2 and the shunt resistor Rs and the ground line, and the voltage between the resistor R1 and the resistor R2 is supplied to the first processor 14.

The noninverting input terminal of the amplifier 13 is connected between the shunt resistor Rs and the heater HT, and the series circuit of the shunt resistor Rs and the heater HT is connected between the output terminal VOUT of the voltage conversion circuit 12 and the minus terminal of the first power supply BAT1. That is, a voltage obtained by dividing the detection voltage V2 (the voltage obtained by subtracting a forward voltage Vf of the diode BE to be described later therefrom) by the shunt resistor Rs and the heater HT is input to the noninverting input terminal of the amplifier 13. Since the resistance value $R_{HTR}$ changes in accordance with the temperature of the heater HT, according to the arrangement example of the electrical components 110 of the controller 102 shown in FIG. 2, the amplifier 13 can output the output voltage $V_{AMP}$ that changes in accordance with the temperature of the heater HT.

In order to detect the resistance value $R_{HTR}$ of the heater HT, the switch Q1 is turned off and the switch Q2 is turned on. In this embodiment, after the switch Q1 is turned on to supply power to the heater HT in accordance with an atomization request from the user, the switch Q2 is turned on and then the switch Q1 is turned off. At this time, letting Vf be the forward voltage of the diode BE and $I_{HTR}$ be the current flowing through the heater HT, the resistance value $R_{HTR}$ of the heater HT is expressed by equation (1):

$$R_{HTR}=V_{HTR}/I_{HTR}=V_{HTR}\cdot(R_{HTR}+R_S)/(V2-Vf) \quad (1)$$

By modifying equation (1), equation (2) giving the resistance value $R_{HTR}$ is obtained:

$$R_{HTR}=R_S\cdot V_{HTR}/(V2-Vf-V_{HTR}) \quad (2)$$

If the amplifier 13 of the detection unit has an amplification factor A, the output voltage $V_{AMP}$ of the amplifier 13 is given by equation (3):

$$V_{AMP}=A\cdot V_{HTR} \quad (3)$$

By modifying equation (3), equation (4) giving the voltage $V_{HTR}$ of the heater HT is obtained:

$$V_{HTR}=V_{AMP}/A \quad (4)$$

Thus, the resistance value Rum of the heater HT can be obtained according to equation (2) and equation (4). Note that the switch Q2 is turned off after the output voltage $V_{AMP}$ of the amplifier 13 used to detect the resistance value $R_{HTR}$ of the heater HT is obtained.

The energization control unit that controls energization of the heater HT can include the first processor 14. The first processor 14 can be formed by, for example, an MCU (Micro Controller Unit), but may be formed by an MCU and an analog circuit. The first processor 14 generates a control signal for controlling energization of the heater HT in accordance with the information obtained by the above-described detection unit (here, the output voltage $V_{AMP}$ of the amplifier 13). The control signal can be, for example, a signal for controlling opening/closing of the switch Q1, but can include another control signal (for example, a control signal for controlling the display unit 116a). The control signal may be, for example, a control signal for suppressing overheating of the heater HT, or may be a control signal for converging the temperature of the heater HT to a target temperature. Based on the voltage generated in a resistor RD arranged on the line connecting the minus terminal of the first power supply BAT1 and the heater HT (second electrical contact C2), the first processor 14 can detect a current flowing through the resistor RD, that is, the current of the heater HT. If an overcurrent is detected in the heater HT, the first processor 14 can perform a process of stopping the energization of the heater HT by turning off the switch Q1, or the like.

Based on the resistance value $R_s$, the voltage Vf, the voltage V2, and the output voltage $V_{AMP}$ of the amplifier 13, the first processor 14 can calculate the resistance value $R_{HTR}$ of the heater HT according to the above-described equation (2) and equation (4). The resistance value $R_s$, the voltage Vf, and the voltage V2 are known values. Then, the first processor 14 calculates an estimated temperature $T_{HTR}$ of the heater HT according to following equation (5). The first processor 14 can control opening/closing of the switch Q1 based on the calculated estimated temperature $T_{HTR}$ so that the temperature of the heater HT matches or converges to the target temperature.

$$T_{HTR}=T_{ref}+(1/\alpha)\cdot(R_{HTR}-R_{ref})\cdot(1/R_{ref})\cdot10^6 \quad (5)$$

In equation (5), $T_{ref}$ is the reference temperature of the heater HT. $R_{ref}$ is the reference resistance value of the heater HT, and this is the resistance value $R_{HTR}$ of the heater HT at the reference temperature. α is the temperature coefficient [ppm/° C.] of the heater HT, and this is a known value. Here, the reference temperature can be an arbitrary temperature, and can be stored in a memory of the first processor 14 in association (linking) with the reference resistance value. As the reference temperature, the preset temperature may be used, or the temperature of the heater HT obtained upon acquiring the reference resistance value may be used. The temperature of the heater HT obtained upon acquiring the reference resistance value may be obtained by applying the estimated temperature $T_{HTR}$ of the heater HT newly calculated using the above-described equations (1) to (5), or may be obtained by converting the output of the sensor (for example, a temperature sensor TM) that detects the temperature of an arbitrary portion in the inhalation device 100.

The electrical components 110 of the controller 102 can further comprise a charging circuit for controlling charging of the first power supply BAT1 by the external power supply 200 when the first connector PG1 of the controller 102 is connected to the second connector PG2 of the external power supply 200. The charging circuit can include, for example, a bridge circuit BC, a protection circuit 15, switches Q3 and Q4, and a diode SD. The bridge circuit BC is a circuit that allows the controller 102 and the external power supply 200 to operate normally even if the electrical contacts A to G of the first connector PG1 are inverted and connected to the electrical contacts G to A of the second connector PG2, respectively. The bridge circuit BC can be formed by, for example, four diodes or transistors. The protection circuit 15 is a circuit for preventing an overcurrent from flowing to the first power supply BAT1 of the controller 102 from the external power supply 200 via the first connector PG1 and the second connector PG2.

Each of the switches Q3 and Q4 includes, for example, a field effect transistor (FET), and opening/closing (ON/OFF) of the switches Q3 and Q4 can be controlled by the first processor 14. That is, it can be said that the first processor 14 controls charging to the first power supply BAT1 of the controller 102 by the external power supply 200. The switches Q3 and Q4 are arranged in series on the line connecting the bridge circuit BC and the plus terminal of the first power supply BAT1, and the voltage of the line connecting the switch Q3 and the switch Q4 can be supplied to a power supply terminal VP of the first processor 14. The diode SD is, for example, a Schottky barrier diode, and can be arranged in parallel with the switch Q3. Since the forward voltage of the Schottky barrier diode tends to be smaller than the forward voltage of the body diode, the Schottky barrier diode enables highly efficient power supply from the first power supply BAT1 to the power supply terminal VP of the first processor 14. Note that the diode added to each of the switches Q3 and Q4 in FIG. 2 represents the body (parasitic) diode of the field effect transistor. The first processor 14 may perform dropper control in which, by controlling ON/OFF of the switch Q3, power unnecessary for charging the first power supply BAT1 is discarded as heat from the power supplied from the first connector PG1. When the first processor 14 performs the dropper control using the switch Q3, it is possible to highly control the charging of the first power supply BAT1 without using a dedicated charging IC or the like.

The electrical components 110 of the controller 102 can further comprise a switch circuit 16 and a protection circuit 17. The switch circuit 16 is a circuit that enables communication between the first processor 14 and a second processor 32 of the external power supply 200 when the first connector PG1 is connected to the second connector PG2 and a predetermined voltage is applied to the EN terminal. The protection circuit 17 detects, based on the voltage generated in a resistor $R_p$ arranged on the line connecting the minus terminal of the first power supply BAT1 and the heater HT (second electrical contact C2), the current flowing to the resistor $R_p$, that is, the current of the heater HT. If an overcurrent is detected in the heater HT, the protection circuit 17 performs a process of stopping the energization of the heater HT, or the like. For example, a switch circuit SP formed by field effect transistors or the like is provided on the line connecting the minus terminal of the first power supply BAT1 and the heater HT (second electrical contact C2). If an overcurrent is detected, the protection circuit 17 can stop the energization of the heater HT by turning off the switch circuit SP. Note that the protection circuit 17 can be configured to operate independently of control of the first processor 14.

The electrical components 110 of the controller 102 can further comprise an LED driving circuit 18, a voltage conversion circuit 20, a puff sensor 21, a touch sensor 22, and the temperature sensor TM. The LED driving circuit 18 drives an LED 19 that forms the display unit 116a of the user interface 116. The voltage conversion circuit 20 includes, for example, a linear regulator such as an LDO (Low DropOut) regulator. The voltage conversion circuit 20 converts the voltage $Vb_1$ supplied from the plus terminal of the first power supply BAT1 into a voltage to be input to the switch 16 and the puff sensor 21, and outputs it. The puff sensor 21 (for example, a pressure sensor or a microphone condenser) detects a puff operation of the user, and supplies the detection signal to the first processor 14. The detection of the puff operation using the puff sensor 21 is a specific example of the atomization request described above. The touch sensor 22 forms the operation unit 116b of the user interface 116. If an operation (for example, a touch operation) by the user is detected, the touch sensor 22 supplies the detection signal to the first processor 14. The touch operation on the touch sensor 22 is a specific example of the atomization request described above. The temperature sensor TM is provided to detect the temperature of the first power supply BAT1, and can include, for example, a thermistor whose resistance value changes in accordance with the temperature. The first processor 14 measures the voltage divided by a resistor R5 connected in series with the thermistor serving as the temperature sensor TM and the thermistor to obtain the resistance value of the thermistor. Based on the resistance value of the thermistor, the first processor 14 can calculate the temperature of the first power supply BAT1. Preferably, the temperature sensor TM is installed near the first power supply BAT1 or on the surface of the first power supply BAT1.

Here, in the example shown in FIG. 2, the line connecting the bridge circuit BC (protection circuit 15) and the switch Q4 and the ground line are connected via the resistors R3 and R4. The voltage between the resistor R3 and the resistor R4 can be input to the EN terminal of the switch circuit 16 and a voltage detection terminal VD (first voltage detection terminal) of the first processor 14. The voltage detection terminal VD of the first processor 14 is a terminal for detecting whether a voltage VBUS of a power supply unit 33 of the external power supply 200 is applied (that is, whether power is supplied from the external power supply 200). If a voltage equal to or higher than a predetermined threshold value is detected at the voltage detection terminal VD, the first processor 14 can determine that the voltage $V_{BUS}$ is applied. The voltage $Vb_1$ supplied from the plus terminal of the first power supply BAT1 can be input to the first processor 14 via resistors R6 and R7. The voltage between the resistor R6 and the resistor R7 can also be input to the first processor 14.

Next, the arrangement example of the electrical components 210 of the external power supply 200 will be described. The electrical components 210 can include, for example, the second power supply BAT2, a voltage conversion circuit 31, the second processor 32, and the power supply unit 33. The voltage conversion circuit 31 includes, for example, a linear regulator such as an LDO (Low DropOut) regulator. The voltage conversion circuit 31 converts a voltage $Vb_2$ supplied from the plus terminal of the second power supply BAT2 into a voltage Vs to be input to a power supply terminal VP of the second processor 32, and outputs it from an output terminal VOUT. That is, the voltage conversion circuit 31 functions as the voltage source of the second processor 32, and the output terminal VOUT of the voltage conversion circuit 31 can be connected to the power supply terminal VP of the second processor 32. The second processor 32 controls power supply from the second power supply BAT2 to the controller 102 by supplying a control signal to the power supply unit 33 and controlling the power supply unit 33. The second processor 32 can be formed by, for example, an MCU (Micro Controller Unit), but may be formed by an MCU and an analog circuit. The power supply unit 33 includes, for example, a DC/DC converter. The power supply unit 33 converts the voltage $Vb_2$ supplied from the plus terminal of the second power supply BAT2 into the voltage $V_{BUS}$, which is used to supply power to the first power supply BAT1 of the controller 102, and outputs it from an output terminal VOUT.

A resistor R8 (first resistor) is provided on the line connecting the output terminal VOUT of the voltage conversion circuit 31 and the electrical contact D of the second connector PG2. When the first connector PG1 is connected to the second connector PG2, the electrical contact D of the second connector PG2 contacts the electrical contact D of the first connector PG1, and can be connected to the ground line via a resistor R9 (second resistor) of the electrical components 110 of the controller 102. The voltage of the line connecting the resistor R8 and the electrical contact D of the second connector PG2 can be input to an input terminal VIN (second voltage detection terminal) of the second processor 32. In other words, the voltage obtained by dividing the voltage Vs by the resistor R8 and the resistor R9 can be input to the input terminal VIN (second voltage detection terminal) of the second processor 32. In accordance with the change in voltage input to the input terminal VIN, the second processor 32 can detect (determine) whether the first connector PG1 is connected to the second connector PG2. The second processor 32 can control the power supply unit 33 in accordance with the connection between the first connector PG1 and the second connector PG2. For example, if the connection between the first connector PG1 and the second connector PG2 is detected, the second processor 32 can supply, to the power supply unit 33 (CE terminal), a control signal for starting power supply from the second power supply BAT2 to the controller 102. Here, the resistance value of the resistor R8 is preferably larger than that of the resistor R9. As an example, the resistance value of the resistor R8 is 1 MΩ, and the resistance value of the resistor R9 is 100 kΩ. At this time, the input voltage at the power supply terminal of the second processor 32 is equal to the voltage applied to the resistors R8 and R9 connected in series. In other words, at this time, the input voltage at the power supply terminal of the second processor 32 is the voltage Vs.

Here, the linear regulator included in the voltage conversion circuit 20 of the controller 102 and the linear regulator included in the voltage conversion circuit 31 of the external power supply 200 may be similar in the specifications (for example, the same model). In this case, the procurement cost for components (for example, the linear regulators) can be reduced. Further, the linear regulator included in the voltage conversion circuit 12 of the controller 102 and the linear regulator included in the voltage conversion circuit 31 of the external power supply 200 may be different in the specifications (for example, the different model). For example, the linear regulator included in the voltage conversion circuit 12 of the controller 102 may have higher performance than the linear regulator included in the voltage conversion circuit 31 of the external power supply 200. With this, it is possible to control highly accurately the energization control of the heater HT. The linear regulator having high performance refers to a linear regulator which can output a wide range of voltage, or whose operation frequency is high.

Figure 3A:
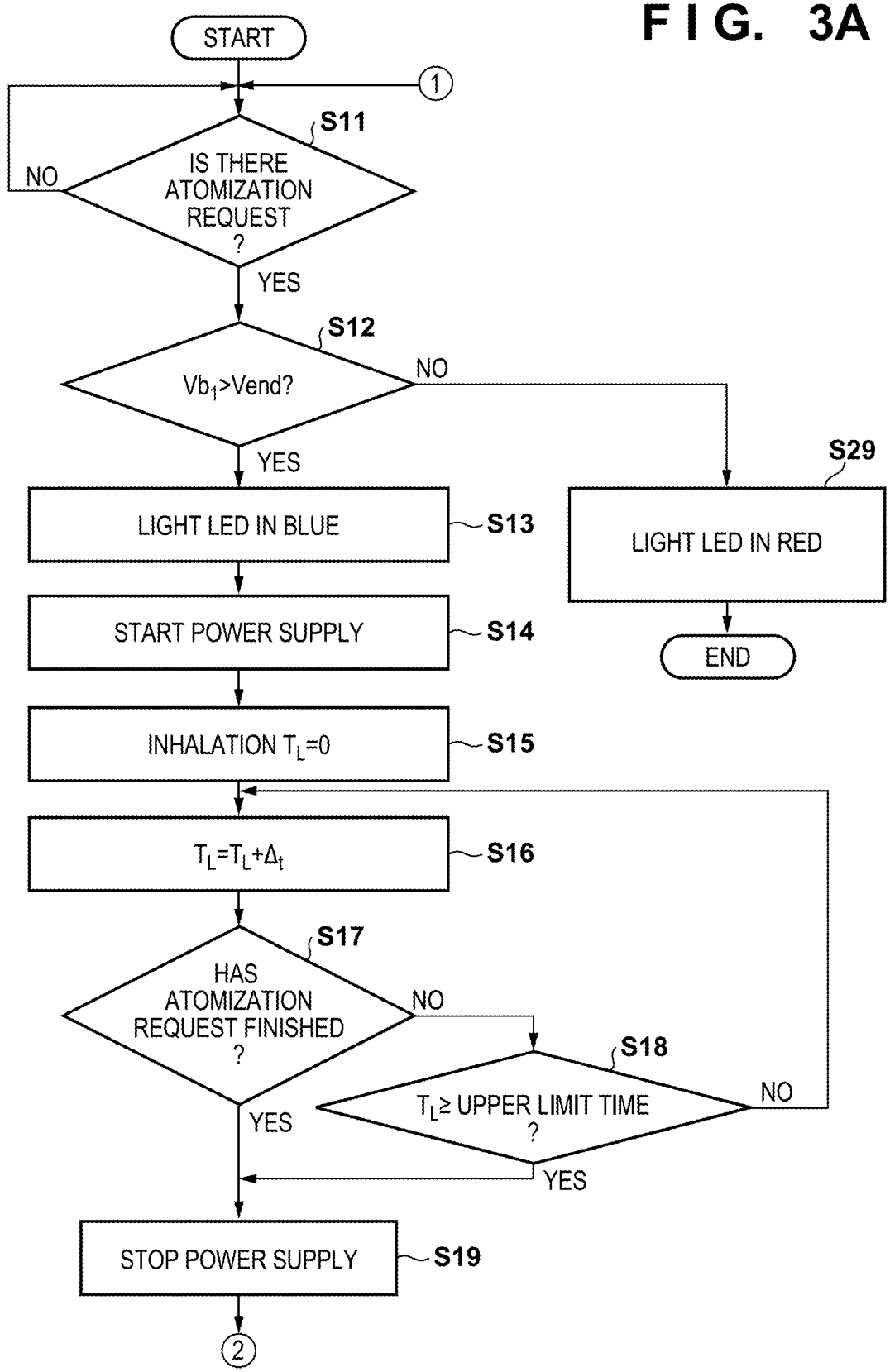
FIGS. 3A and 3B are flowcharts illustrating an operation example of an inhalation device.
Figure 3B:
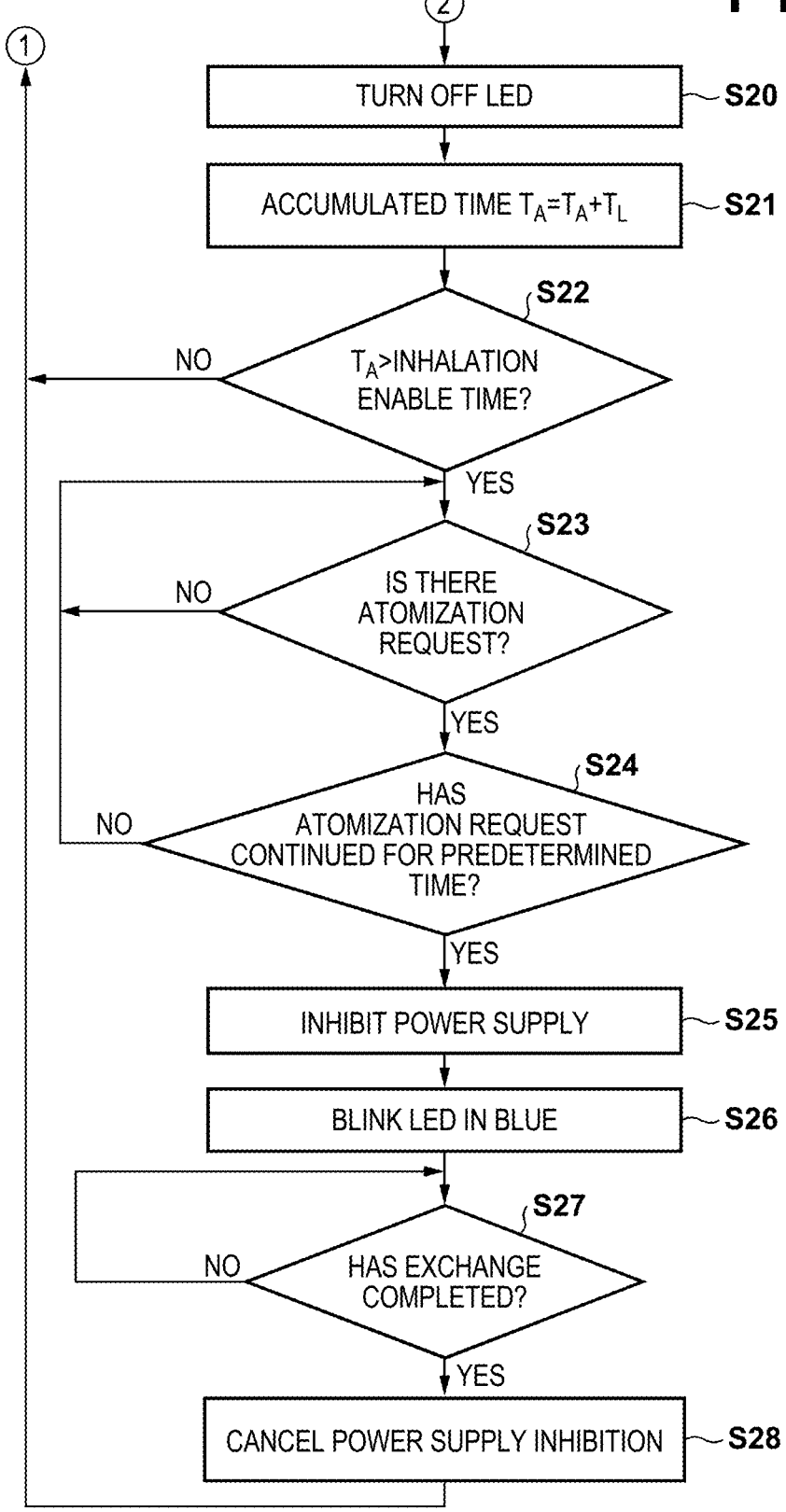

FIGS. 3A and 3B illustrate an operation example of the inhalation device 100. This operation is a process (atomization process) of heating the aerosol source by the heater HT in accordance with an atomization request from the user and providing the atomized aerosol source from the mouthpiece port 130, and controlled by the first processor 14. The first processor 14 includes a memory storing programs, and a CPU that operates in accordance with the programs.

In step S11, the first processor 14 waits for reception of an atomization request (more specifically, a detection signal transmitted from the puff sensor 21 and/or the touch sensor 22). If the atomization request is received, the first processor 14 executes step S12. The atomization request is a request to operate the atomizer 104, more specifically, a request to control the heater HT within a target temperature range so as to generate an aerosol from the aerosol source. The atomization request can be an operation of detecting by the puff sensor 21 that the user has performed an inhalation operation (puff operation) through the mouthpiece port 130, and notifying the first processor 14 of the detection by the puff sensor 21 (for example, transmission of a detection signal). Alternatively, the atomization request can be an operation of notifying, by the operation unit 116b, the first processor 14 that the user has operated the operation unit 116b (touch sensor 22) (for example, transmission of an operation signal). Hereinafter, during the inhalation operation by the user or during the operation of the operation unit 116b by the user, the atomization request is continuously transmitted from the puff sensor 21 or the operation unit 116b, and the atomization request (transmission thereof) ends when the user terminates the inhalation operation or the operation of the operation unit 116b.

In step S12, the first processor 14 obtains the voltage $Vb_1$ of the first power supply BAT1 from a power supply management circuit (not shown), and determines whether the voltage $Vb_1$ exceeds a discharge end voltage Vend (for example, 3.2 V). If the voltage $Vb_1$ is equal to or lower than the discharge end voltage Vend, this means that the dischargeable remaining amount of the first power supply BAT1 is insufficient. Accordingly, if the voltage $Vb_1$ is equal to or lower than the discharge end voltage Vend, the process advances to step S29, and the first processor 14 gives a notification to prompt charging of the first power supply BAT1 by using the display unit 116a (LED 19) of the user interface 116. For example, this notification can be lighting in red or blinking the LED 19 included in the display unit 116a. When the notification is given, the user inserts the inhalation device 100 (controller 102) into the accommodation portion 201 of the external power supply 200, and connects the first connector PG1 of the controller 102 to the second connector PG2 of the external power supply 200. With this, the first power supply BAT1 of the controller 102 is charged by the external power supply 200, and the dischargeable remaining amount can be increased. On the other hand, if the voltage $Vb_1$ exceeds the discharge end voltage Vend in step S12, the first processor 14 performs a heating process. The heating process is a process of controlling the switch Q1 to supply power to the heater HT in accordance with the reception of the atomization request of the aerosol source, thereby heating the aerosol source. The heating process can include steps S13 to S17.

In step S13, the first processor 14 can notify, using the display unit 116a (LED 19) of the user interface 116, that a normal operation is possible. For example, this notification can be lighting, in blue, of the LED 19 included in the display unit 116a. Then, in step S14, the first processor 14 starts power supply control of the heater HT. The power supply control of the heater HT includes temperature control of controlling the heater HT within the target temperature range. The temperature control can include feedback control of calculating the estimated temperature $T_{HTR}$ of the heater HT by detecting the resistance value $R_{HTR}$ of the heater HT, and controlling opening/closing of the switch Q1 based on the estimated temperature $T_{HTR}$ such that the temperature of the heater HT falls within the target temperature range (for example, the temperature of the heater HT matches or converges to the target temperature).

Then, in step S15, the first processor 14 resets an inhalation time $T_L$ to 0. After that, in step S16, the first processor 14 adds Δt to the inhalation time $T_L$. At corresponds to the time interval between the execution of step S16 and the next execution of step S16.

Then, in step S17, the first processor 14 determines whether the atomization request has finished. If the atomization request has finished, the first processor 14 advances to step S19, and stops the power supply control of the heater HT. On the other hand, if the atomization request has not finished, the first processor 14 advances to step S18, and determines whether the inhalation time $T_L$ has reached the upper limit time. If the inhalation time $T_L$ has not reached the upper limit time, the first processor 14 returns to step S16. If the inhalation time $T_L$ has reached the upper limit time, the first processor 14 advances to step S19. As an example, the upper limit time may be between 2.0 and 2.5 sec.

After step S19, in step S20, the first processor 14 turns off the LED 19 which has been lit in blue. The order of step S19 and step S20 may be reversed, or the first processor 14 may simultaneously execute steps S19 and S20. Then, in step S21, the first processor 14 updates an accumulated time $T_A$. More specifically, the inhalation time $T_L$ is added to the current accumulated time $T_A$ in step S21. The accumulated time $T_A$ can be the accumulated time of the capsule 106 used for inhalation. In other words, the accumulated time $T_A$ can be the accumulated time of inhalation of the aerosol via the flavor source 131 of the capsule 106.

In step S22, the first processor 14 determines whether the accumulated time $T_A$ does not exceed the inhalation enable time (for example, 120 sec). If the accumulated time $T_A$ does not exceed the inhalation enable time, this means that the capsule 106 can still provide the flavor material, so that the process returns to step S11. On the other hand, if the accumulated time $T_A$ exceeds the inhalation enable time, the process advances to step S23, and the first processor 14 waits for generation of an atomization request. If an atomization request is generated, in step S24, the first processor 14 waits for the atomization request to continue for a predetermined time. Thereafter, in step S25, the first processor 14 inhibits the power supply control of the heater HT. Note that step S24 may be omitted.

Then, in step S26, the first processor 14 gives a notification to prompt an exchange of the capsule 106 by using the display unit 116a of the user interface 116. For example, this notification can be blinking (repetition of turning on and off), in blue, of the LED 19 included in the display unit 116a. When the notification is given, the user can exchange the capsule 106. In an example, one atomizer 104 and a plurality of (for example, three) capsules 106 can be sold as one set. In such an example, after the one atomizer 104 and all the capsules 106 included in one set are consumed, the atomizer 104 and the last capsule 106 included in the consumed set can be exchanged with the atomizer 104 and the capsule 106 included in a new set. The order of step S25 and step S26 may be reversed, or the first processor 14 may simultaneously execute steps S25 and S26.

In step S27, the first processor 14 waits for completion of the exchange of the capsule 106 (or the capsule 106 and the atomizer 104). After the exchange of the capsule 106 is completed, the process advances to step S28, and the first processor 14 cancels the inhibition of the power supply control of the heater HT and returns to step S11.

In the aerosol generation system described above, the first processor 14 of the controller 102 and the second processor 32 of the external power supply 200 can perform processes different from each other. In this case, operating the first processor 14 and the second processor 32 in similar manners can be disadvantageous in terms of power saving of the aerosol generation system. When each of the first processor 14 and the second processor 32 is formed by the MCU, as the voltage applied to the power supply terminal VP of each processor is increased, the operation frequency corresponding to the process speed is improved. Further, in such a case, as the voltage applied to the power supply terminal VP of each processor is increased, power saving is improved. Therefore, in this embodiment, the first voltage applied to the power supply terminal VP of the first processor 14 and the second voltage applied to the power supply terminal VP of the second processor 32 are set to be different from each other. For example, one of the first processor 14 and the second processor 32 that is performing a predetermined process is applied, to its power supply terminal VP, with a voltage that can ensure the process speed in the predetermined process. On the other hand, the other one of the first processor 14 and the second processor 32 is applied, to its power supply terminal VP, with a voltage lower than the power supply voltage applied to the processor performing the predetermined process, thereby achieving low power consumption.

In this embodiment, the first processor 14 performs the heating process of heating the heater HT by controlling the switch Q1, the temperature calculation process of calculating the estimated temperature $T_{HTR}$ of the heater HT by controlling the switch Q2, and/or the charging control process of controlling charging of the first power supply BAT1 by controlling the switches Q3 and Q4. Therefore, the first voltage that can ensure the process speed (for example, clock frequency) required in the heating process, the temperature calculation process, and/or the charging control process can be applied to the power supply terminal VP of the first processor 14. On the other hand, the second processor 32 performs a process of controlling power supply (for example, the start and/or end of power supply) to the controller 102 by controlling the power supply unit 33. This process may be performed at a process speed lower than the process speed required for the process performed by the first processor 14. Accordingly, by setting the second voltage applied to the power supply terminal VP of the second processor 32 lower than the first voltage applied to the power supply terminal VP of the first processor 14, low power consumption can be achieved. Here, for example, if the second processor 32 performs the charging control process of controlling charging of the first power supply BAT1 by controlling the switches Q3 and Q4, during the charging, the second voltage applied to the power supply terminal VP of the second processor 32 may be set higher than the first voltage applied to the power supply terminal VP of the first processor 14.

By increasing the first voltage applied to the power supply terminal VP of the first processor 14, opening/closing (ON/OFF) of each of the switches Q1 and Q2 can be switched at high speed. Thus, the first processor 14 can perform the temperature calculation process in a very short time during the heating process. Since performing the temperature calculation process in a very short time has only a minor influence or hardly any influence on the heating process, it is possible to provide the user with an intended flavored aerosol. Further, if the temperature calculation process can be performed in a very short time, it is possible to calculate the estimated temperature $T_{HTR}$ of the heater HT highly frequently during the heating process. This can improve the accuracy of the heating process and suppress overheating of the heater HT, so that it is possible to provide the user with an intended flavored aerosol.

The external power supply 200 is mainly used to charge the first power supply BAT1 of the inhalation device 100 by the second power supply BAT2. If the first voltage applied to the power supply terminal VP of the second processor 32 is lowered, the less power stored in the second power supply BAT2 is consumed by the second processor 32. Thus, the second power supply BAT2 can charge the first power supply BAT1 with more power. In other words, the amount of aerosol providable to the user per one charging of the second power supply BAT2 increases, and this can improve the merchantability of the aerosol generation system.

Figure 4:
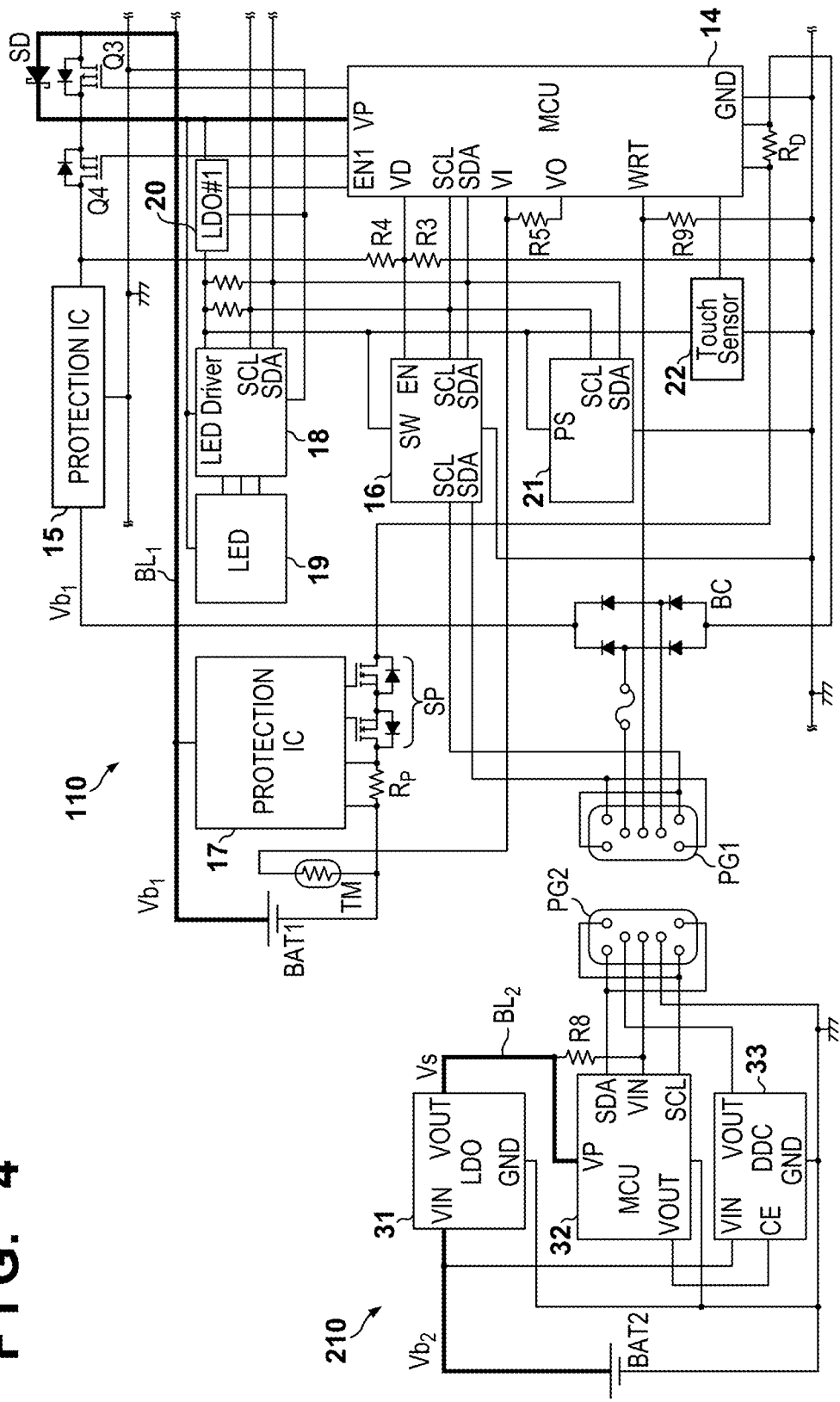
FIG. 4 is a view for explaining the power supply voltages of a first processor and a second processor.
Figure 5:
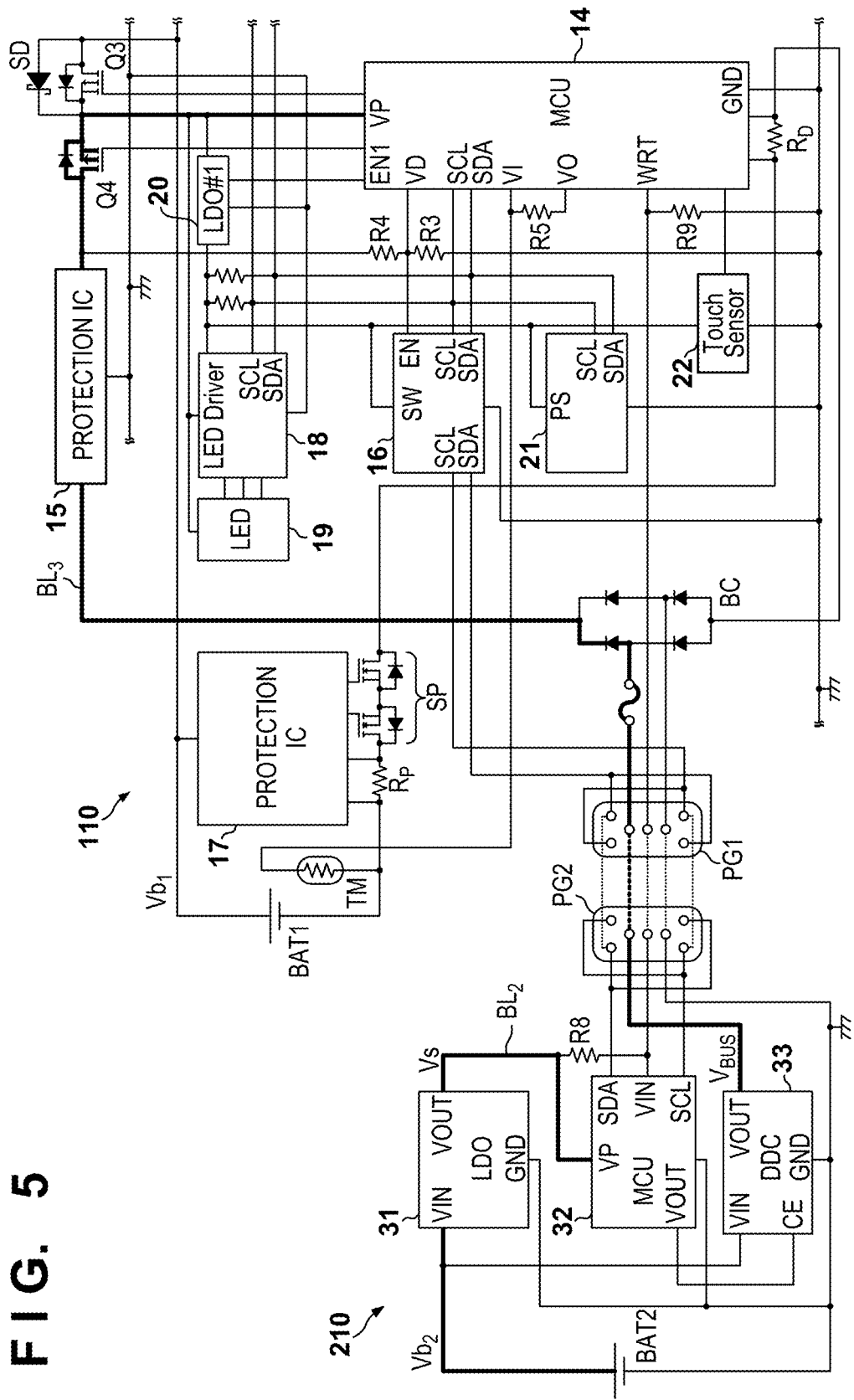
FIG. 5 is a view for explaining the power supply voltages of the first processor and the second processor.

With reference to FIGS. 4 and 5, the line (path) for applying the first voltage to the power supply terminal VP of the first processor 14 and the line (path) for applying the second voltage to the power supply terminal VP of the second processor 32 will be described below. FIGS. 4 and 5 show an arrangement example of the electrical components 110 of the controller 102 and the electrical components 210 of the external power supply 200. The arrangement example shown in FIGS. 4 and 5 is similar to the arrangement example shown in FIG. 2, but the arrangement on the right side of the first processor 14 (the circuit arrangement for supplying power to the heater HT) is not illustrated. Each bold line in FIGS. 4 and 5 indicates the portion to pay attention to in the description of the voltage applied to the power supply terminal VP of the first processor 14 and/or the power supply terminal VP of the second processor 32. FIG. 4 shows an unconnected state in which the first connector PG1 of the controller 102 is not connected to the second connector PG2 of the external power supply 200, and FIG. 5 shows a connected state in which the first connector PG1 is connected to the second connector PG2.

First, the unconnected state in which the first connector PG1 is not connected to the second connector PG2 will be described with reference to FIG. 4. In the unconnected state, as indicated by a bold line $BL_1$ in FIG. 4, a voltage (first voltage) can be applied to the power supply terminal VP of the first processor 14 via the first line connecting the plus terminal of the first power supply BAT1 and the power supply terminal VP of the first processor 14. On the other hand, as indicated by a bold line $BL_2$ in FIG. 4, a voltage (second voltage) can be applied to the power supply terminal VP of the second processor 32 via the second line connecting the plus terminal of the second power supply BAT2 and the power supply terminal VP of the second processor 32. The voltage conversion circuit 31 is provided on the second line $BL_2$. The voltage conversion circuit 31 is configured to output, from the output terminal VOUT, the voltage Vs lower than the first voltage applied to the power supply terminal VP of the first processor 14, and the voltage Vs output from the output terminal VOUT of the voltage conversion circuit 31 can be input (applied) to the power supply terminal VP of the second processor 32. With this, the power consumption of the second processor 32 can be made lower than that of the first processor 14.

Here, only the diode SD is arranged in the forward direction on the first line $BL_1$, and no component that causes a larger voltage drop than the voltage conversion circuit 31 is arranged thereon. Thus, it is possible to reduce a voltage loss (voltage drop) on the first line $BL_1$, and apply, as the first voltage, the voltage almost equal to the output voltage $Vb_1$ of the first power supply BAT1 to the power supply terminal VP of the first processor 14. Note that it is also conceivable to form the first line by turning on the switch Q3 including no body diode instead of using the diode SD. However, in this case, if the switch Q4 is turned off, the output voltage $Vb_1$ of the first power supply BAT1 is not applied to the power supply terminal VP of the first processor 14. Therefore, during charging of the first power supply BAT1 and the manufacture of the inhalation device 100, it is necessary to apply a voltage to the power supply terminal VP of the first processor 14 from a voltage source other than the first power supply BAT1. It is further conceivable to use the body diode of the switch Q3 without turning on the switch Q3 but, in terms of avoiding a voltage loss on the first line, providing the diode SD having a lower forward resistance than the body diode is preferable. In addition, a current (backflow) flowing from the power supply terminal VP of the first processor 14 toward the first connector PG can be prevented by the body diode of the switch Q4.

Next, the connection state in which the first connector PG1 is connected to the second connector PG2 will be described with reference to FIG. 5. As has been described above, when the first connector PG1 is electrically connected to the second connector PG2, the input terminal VIN (voltage detection terminal) of the second processor 32 is connected to the resistor R9 of the controller 102, and the voltage applied to the input terminal VIN of the second processor 32 changes (changes from High level to Low level). Triggered by the change in voltage at the input terminal VIN, the second processor 32 supplies, to the power supply unit 33 (CE terminal), a control signal for starting power supply from the second power supply BAT2 to the controller 102. With this, the voltage $V_{BUS}$ is output from the output terminal VOUT of the power supply unit 33.

When the voltage $V_{BUS}$ is output from the output terminal VOUT of the power supply unit 33, the voltage at the voltage detection terminal VD of the first processor 14 changes. Triggered by the change in voltage at the voltage detection terminal VD, the first processor 14 turns on the switches Q3 and Q4. With this, as indicated by a bold line $BL_3$ in FIG. 5, the power supply terminal VP of the first processor 14 in the connection state can be applied with the voltage (third voltage) via the third line connecting the first connector PG1 (output terminal VOUT of the power supply unit 33) and the power supply terminal VP of the first processor 14. On the other hand, the power supply terminal VP of the second processor 32 in the connected state can be input (applied) with the voltage Vs output from the output terminal VOUT of the voltage conversion circuit 31 via the second line $BL_2$, as in the unconnected state. The voltage conversion circuit 31 can be configured to output, from the output terminal VOUT, the voltage Vs lower than the third voltage applied to the power supply terminal VP of the first processor 14. With this, the power consumption of the second processor 32 can be made lower than that of the first processor 14. Note that the voltage drop amount in the voltage conversion circuit 31 may differ between the unconnected state and the connected state, or may not differ therebetween.

The arrangement of the aerosol generation system described above can also be advantageous in a case in which the first processor 14 is restored when the first power supply BAT1 is over-discharged. For example, when the first power supply BAT1 is over-discharged in the unconnected state, the protection circuit 17 of the controller 102 detects the over-discharging, and stops the discharging of the first power supply BAT1 by turning off the switch circuit SP. At this time, the power supply to the power supply terminal VP of the first processor 14 can also be stopped. In order to restore the first processor 14 in this case, for example, the controller 102 can be inserted into the accommodation portion 201 of the external power supply 200 to connect the first connector PG1 to the second connector PG2.

Figure 6:
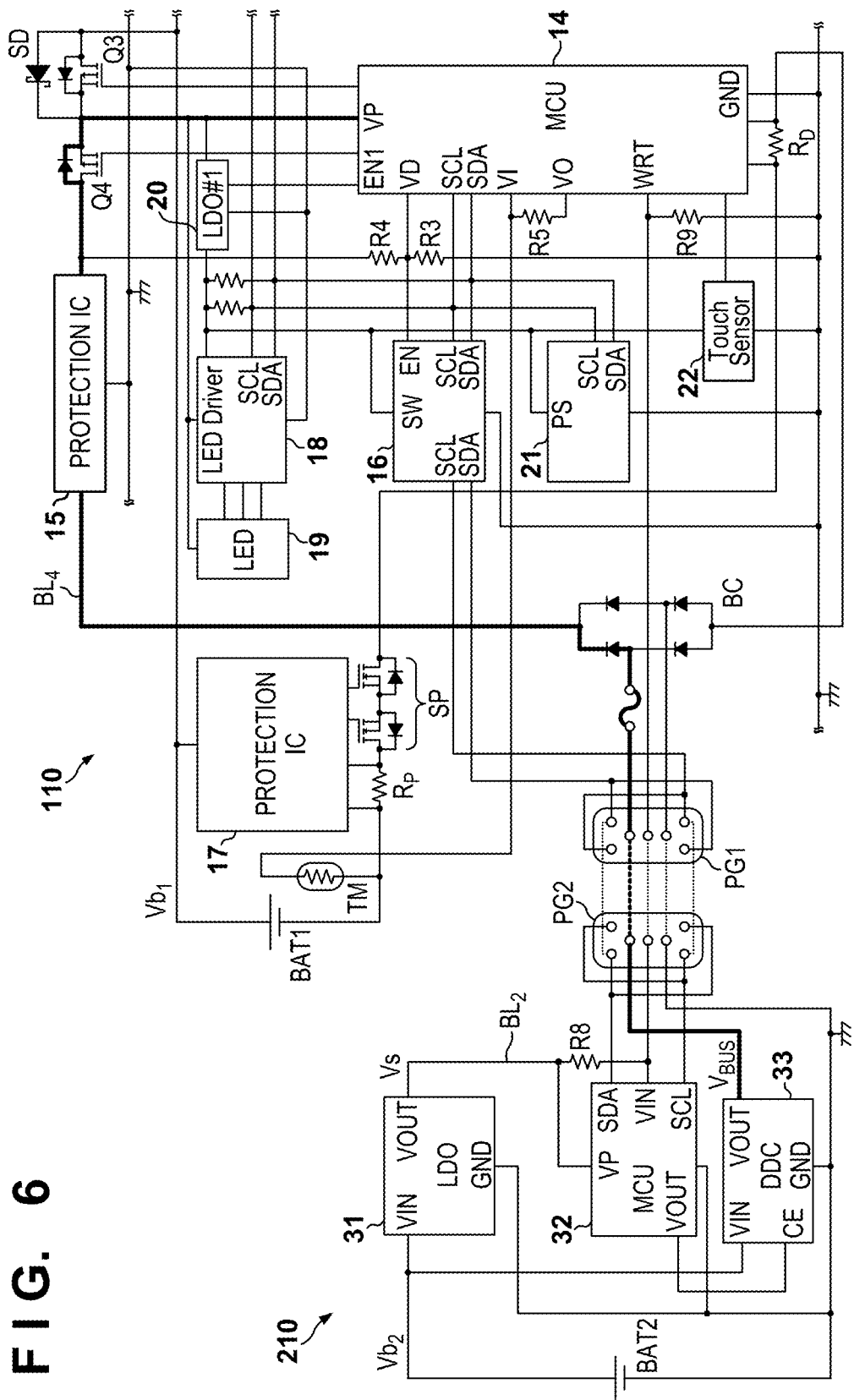
FIG. 6 is a view for explaining the power supply voltages of the first processor and the second processor.

When the first connector PG1 is connected to the second connector PG2, the voltage $V_{BUS}$ is input (applied) from the external power supply 200 (power supply unit 33) to the controller 102 (first connector PG1). At this time, although the switch Q4 is in the OFF state because the first processor 14 is in the stopped state, as indicated by a bold line $BL_4$ in FIG. 6, a line (restoring line) connecting the first connector PG1 and the power supply terminal VP of the first processor 14 can be formed by the body diode of the switch Q4. That is, the voltage $V_{BUS}$ can be applied to the power supply terminal VP of the first processor 14. With this, the first processor 14 can be restored.

Note that the voltage $V_{BUS}$ is about 5.0 V in general, and the output voltage $Vb_1$ of the first power supply BAT1 when using a lithium ion secondary battery as the first power supply BAT1 is about between 4 V and 3 V. That is, the voltage to be supplied to the power supply terminal VP of the first processor 14 changes between a case in which over-discharging of the first power supply BAT1 does not occur and a case in which over-discharging of the first power supply BAT1 occurs. If it is tried that the allowable range of the input voltage at the power supply terminal VP of the first processor 14 includes these two different voltages, this leads to a narrow choice of the first processor 14. However, at the time of restoration, the voltage $V_{BUS}$ is lowered due to the forward voltage drop of the body diode of the switch Q4. Thus, the voltage closer to the output voltage $Vb_1$ of the first power supply BAT1 in the case of no over-discharging can be supplied to the power supply terminal VP of the first processor 14. This can suppress a narrow choice of the first processor 14.

Here, the voltage conversion circuit 20 (LDO) is connected in parallel with the restoring line. Accordingly, it is also possible to operate (restore) the switch circuit 16, the puss sensor 21, and the touch sensor 22, each of which uses the output voltage of the voltage conversion circuit 20 as the power supply voltage. In this case, the first processor 14 can give a notification that the controller 102 (first processor 14) has been restored by using the display unit 116a of the controller 102 and/or the display unit 203a of the external power supply 200. For example, this notification can be lighting or blinking the LED 19 by the LED driving circuit 18, or lighting or blinking the LED included in the display unit 203a of the external power supply 200 by transmitting a signal indicating the restoration to the external power supply 200 via the switch circuit 16.

The invention is not limited to the foregoing embodiments, and various variations/changes are possible within the spirit of the invention.

What is claimed is:

1. An aerosol generation system comprising:
a controller for an inhalation device, the controller including a first power supply, a first connector, and a first processor configured to perform energization control of a heater which is used to heat an aerosol source; and
a power supply device including a second power supply, a second connector which is connected to the first connector at the time of charging of the first power supply, and a second processor configured to perform control of power supply from the second power supply to the controller via the second connector,
wherein a first voltage applied to a power supply terminal of the first processor such that the first processor is capable of performing the energization control and a second voltage applied to a power supply terminal of the second processor such that the second processor is capable of performing the energization control are different from each other.

2. The system of claim 1, wherein
the first voltage is a voltage applied to the power supply terminal of the first processor via a first line connecting the first power supply and the power supply terminal of the first processor.

3. The system of claim 2, wherein
the second voltage is a voltage applied to the power supply terminal of the second processor via a second line connecting the second power supply and the power supply terminal of the second processor.

4. The system of claim 1, wherein
the power supply device includes a linear regulator on a second line connecting the second power supply and the power supply terminal of the second processor.

5. The system of claim 4, wherein
the linear regulator outputs, as the second voltage, a voltage lower than the first voltage.

6. The system of claim 5, wherein
the controller includes, on a first line connecting the first power supply and the power supply terminal of the first processor, no component that causes a larger voltage drop than the linear regulator.

7. The system of claim 1, wherein
the controller comprises a first line connecting the first power supply and the power supply terminal of the first processor, and a third line connecting the first connector and the power supply terminal of the first processor, and
the first processor is configured to be operated by each of power supplied from the first power supply via the first line and power supplied from the power supply device via the third line.

8. The system according to claim 7, wherein
in an unconnected state in which the first connector is not connected to the second connector, the first processor is operated by power supplied from the first power supply via the first line, and
in a connected state in which the first connector is connected to the second connector, the first processor is operated by power supplied from the power supply device via the third line.

9. The system according to claim 1, wherein
during charging of the first power supply by power supplied from the power supply device, a voltage applied to the power supply terminal of one of the first processor and the second processor that controls the charging is higher than a voltage applied to the power supply terminal of the other processor.

10. The system of claim 1, wherein
the power supply device includes a DC/DC converter configured to convert a voltage supplied from the second power supply and output the converted voltage to the second connector.

* * * * *